US00PP24171P3

(12) United States Plant Patent

Olesen et al.

(10) Patent No.: US PP24,171 P3

(45) Date of Patent: Jan. 21, 2014

(54) *CLEMATIS* PLANT NAMED 'EVIPO041'

(50) Latin Name: *Clematis viticella*
Varietal Denomination: Evipo041

(75) Inventors: Mogens Nyegaard Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 13/374,054

(22) Filed: Dec. 9, 2011

(65) Prior Publication Data

US 2013/0152259 P1 Jun. 13, 2013

(51) Int. Cl.
*A01H 5/00* (2006.01)

(52) U.S. Cl.
USPC ..... Plt./228

(58) Field of Classification Search
USPC ..... Plt./228
See application file for complete search history.

(56) References Cited

PUBLICATIONS

GTITM UPOVROM Citation for 'Evipo041' as per QZ PBR 20100224; Feb. 3, 2010.*

* cited by examiner

*Primary Examiner* — Kent L Bell

(57) ABSTRACT

A new *Clematis* plant with a compact growth habit, profuse, light pink flowers, and continuous summer flowering. The variety successfully propagates from softwood cuttings and is suitable for cultivation commercial nursery and glasshouse culture. This new and distinct variety has shown to be uniform and stable in the resulting generations from asexual propagation from vegetative cuttings.

4 Drawing Sheets

Botanical classification:
Genus: *Clematis.*
Species: *viticella.*
Variety denomination: 'Evipo041'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 1996 and the resulting seeds were planted the following winter in a controlled environment in Guernsey, Channel Islands, United Kingdom. The new variety named 'Evipo041' originated as a single seedling from the stated cross.

The new *clematis* plant may be distinguished from its female seed parent mainly by growth habit. The new variety is more compact than the female seed parent.

The new *clematis* plant may be distinguished from its male pollen parent mainly by growh habit. The new variety is more compact than the male pollen parent.

The objective of the hybridization of this *clematis* plant was to create a new and distinct variety for glasshouse and nursery culture with unique qualities such as:

1. Uniform and abundant light pink flowers;
2. Vigorous and compact growth, making the variety suitable for small container culture; and
3. Improved disease resistance.

This combination of qualities was lacking in *clematis* plants that were in commercial cultivation and the qualities have been substantially achieved in the new variety.

'Evipo041' was selected by Mogens N. Olesen and Raymond J. Evison in their *clematis* development program in the Channel Islands, United Kingdom in 1997. Asexual reproduction of 'Evipo041' by means of vegetative cuttings and traditional layering was first performed by Mogens N. Olesen and Raymond J. Evison in the nursery during the summer of 1997. This initial and subsequent asexual propagations have demonstrated that the characteristics of 'Evipo041' are true to type and are transmitted from one generation to the next.

BRIEF DESCRIPTION OF THE DRAWING

The accompanying color illustration show as true as is reasonably possible to obtain in color photographs of this type.

DETAILED DESCRIPTION OF THE VARIETY

Figure 1:
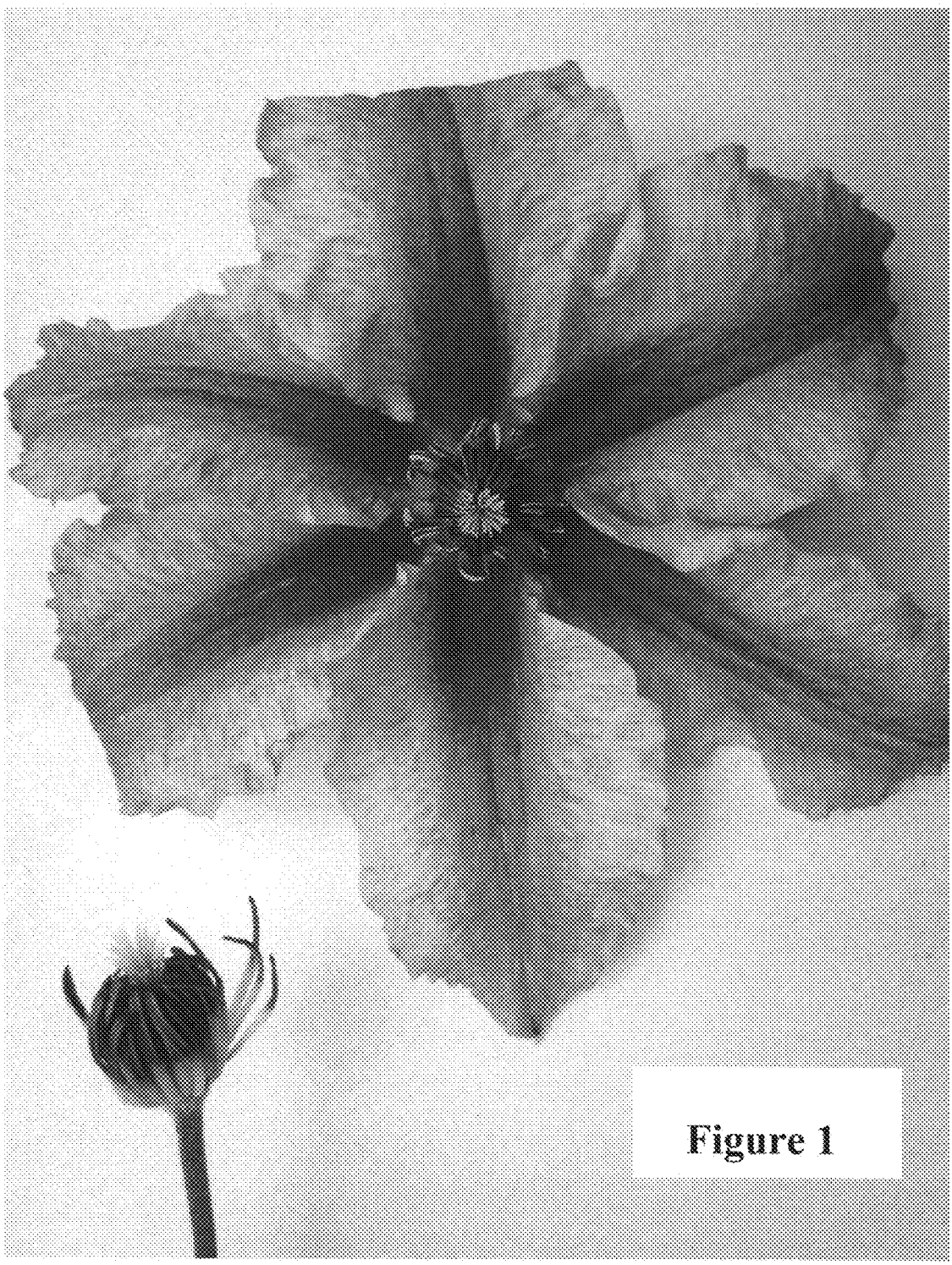
FIG. 1. Open flower and reproductive parts.
Figure 2:
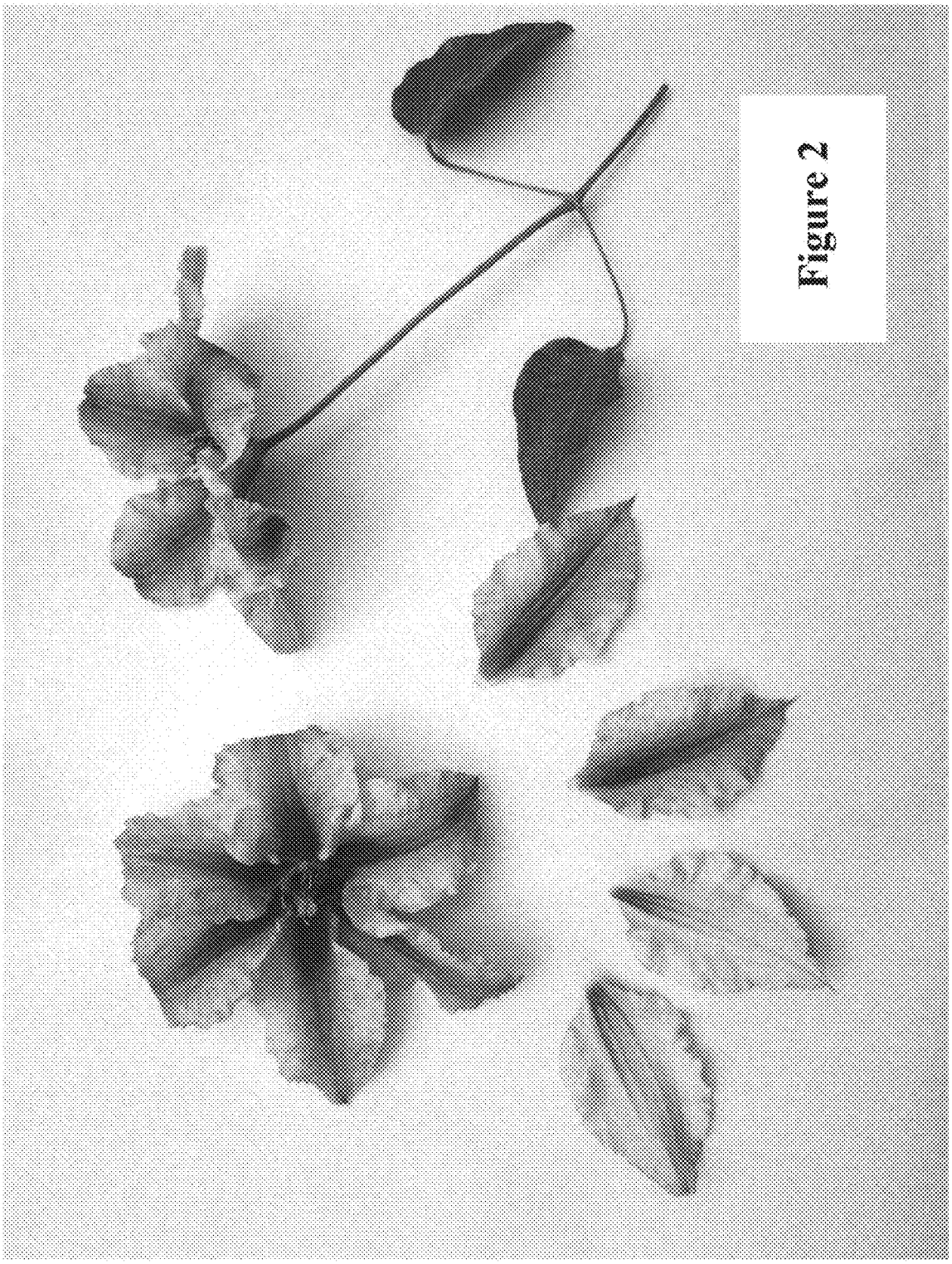
FIG. 2. Open flowers with tepals detached.
Figure 3:
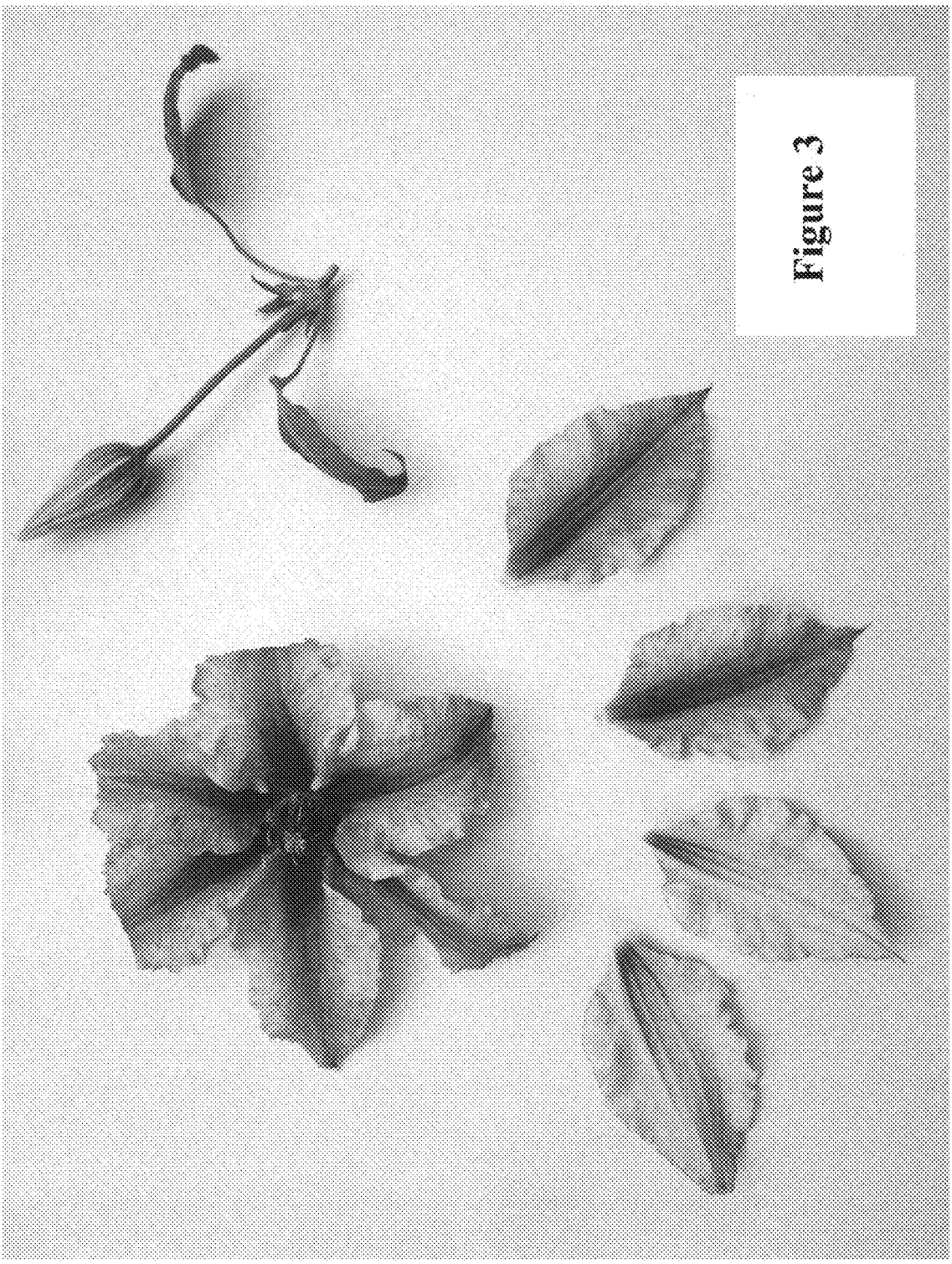
FIG. 3. Open flower and flower bud with tepals detached.
Figure 4:
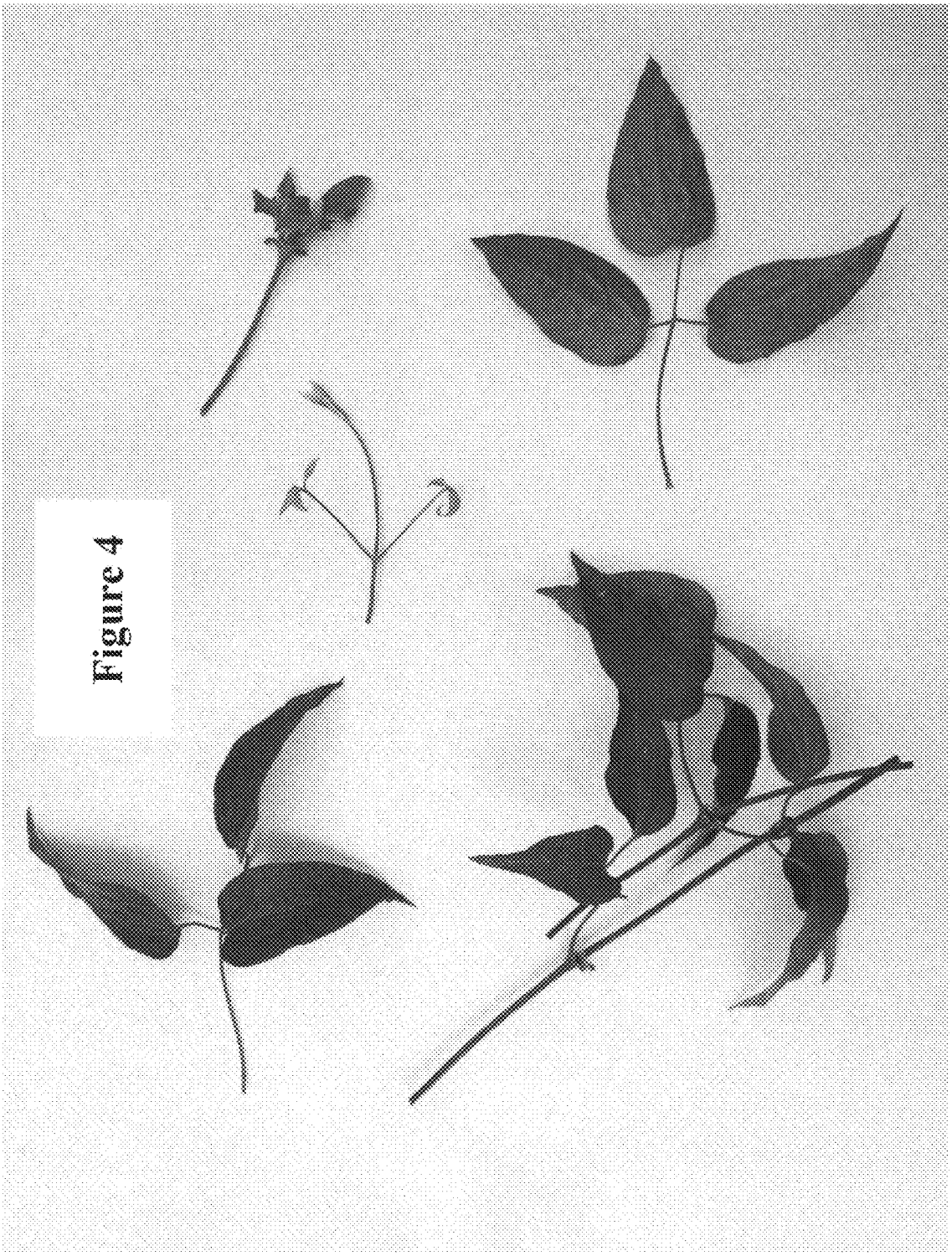
FIG. 4. Stems and leaves.

The following is a detailed description of 'Evipo041', as observed in its growth throughout the flowering period in open air container production in Yamhill County Oreg. Observed plants were cultivated for a period of 24 months in 1 gallon containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo029' described and illustrated in U.S. Plant Pat. No. 16,471 are compared to 'Evipo041' in Chart 1.

CHART 1

| | 'Evipo041' | 'Evipo029' |
|---|---|---|
| Flower diameter | 110 to 160 mm | 70 to 90 mm |
| Tepal color | Upon and after opening, the upper surface is Purple Group 76B with a central bar that is Purple Group N79C. The blending of central bar and margins creates a zone of Purple Group 77B. The lower surface is Purple Group 76C with a central bar of Yellow-Green Group 145C. Within the central bar are 3 parallel veins the color of Purple Group N79C. | Upon opening: Upper surface is Violet Group 85B. After opening: Upper surface is Violet Group 85C. Variations. --Lower surface about Violet Group 85C. and can exhibit light green central bar along each tepal length, the color of Greyed Green Group 190A |
| Tepal count | 6 | 6 to 8 |

FLOWER AND FLOWER BUD

Blooming habit: Continuous. The natural flowering period is generally from May to September.

Flower bud:

*Size.*—Normally 35 mm in length. Bud diameter is 12 mm.

*Bud form.*—Broad based elliptical.

*Bud color.*—Yellow-Green Group 148C with intonations of Greyed-Purple Group 184B.

Pedicel:

*Surface texture.*—Smooth.

*Length.*—45 to 80 mm.

*Color.*—Yellow-Green Group 146C with intonations of Greyed-Purple Group 183B.

*Strength.*—Moderate.

Receptacle:

*Surface texture.*—Very pubescent.

*Shape.*—Broad funnel.

*Size.*—2 mm (h)×4 mm (w).

*Color.*—Yellow-Green Group 144C with intonations of Greyed-Purple Group 183B.

Flower arrangement:

*Location on vine.*—New and old growth.

*Borne.*—Singly and in clusters of 2 to 3 flowers.

Flower bloom:

*Size.*—Flowers are 110 to 160 mm in diameter and 20 mm in depth.

*Profile.*—Open flowers are broad funnel when viewed from the side. The upper portion is flat, lower portion is convex.

*Fragrance.*—None.

*Lasting quality.*—Flowers normally remain 10 days on the plant. As a cut flower, flowers normally last up to 3 days.

Tepals:

*Tepal color.*—Upon and after opening, the upper surface is Purple Group 76B with a central bar that is Purple Group N79C. The blending of central bar and margins creates a zone of Purple Group 77B. The lower surface is Purple Group 76C with a central bar of Yellow-Green Group 145C. Within the central bar are 3 parallel veins the color of Purple Group N79C.

*Quantity.*—Normally 6 tepals.

*Size.*—Young flowers are 55 mm in length by 35 mm wide. As flowers reach full maturity the tepals are 75 mm in length by 45 mm wide.

*Shape.*—Individual tepal shape is elliptic. The tepal apex is acuminate. The tepal base is acute.

*Apex recurvature.*—Slightly curved.

*Tepal cross section.*—Slightly reflexed.

*Margins.*—Entire. Medium undulations of margin observed.

*Persistence.*—Tepals persist.

Reproductive organs:

*Arrangement.*—Somewhat compact.

*Pollen.*—Quantity: Abundant. Color: White Group 155C.

*Anthers.*—Size: 5 mm in length. Color: Purple Group N77A. Quantity: 65 on average.

*Filaments.*—Color: Yellow-Green Group 150D. Length: 6 mm.

*Pistils.*—Quantity: 65 on average.

*Stigmas.*—Superior in location relative to the length of the filaments and the height of the anthers.

*Styles.*—Color: Green Group 138D. Length: 15 mm.

Seed head characteristics: No seed observed.

PLANT

Plant form: Climbing.

Plant growth: Moderately vigorous and compact.

Size: Seasons growth attains 90 cm in height. Average spread is 50 cm.

Hardiness: Trials to date show the variety hardy in USDA Zones 6.

Stems:

*Color.*—Juvenile stems are generally Yellow Group 144A. Other intonations observed are Greyed-Purple Group 185A. Mature stems are Greyed-Orange Group N167B and 166B.

*Internodes.*—10 to 12 cm between nodes.

*Length.*—Normally 40 cm from the base of the plant to the flowering portion of the stem.

*Diameter.*—2.5 mm on average.

*Surface.*—Mature stems are smooth with ribs parallel to the stem.

Plant foliage:

*Leaf characteristics.*—Deciduous.

*Arrangement.*—Trifoliate.

*Leaf size.*—Compound leaves are normally 90 mm (l)× 75 mm (w). Terminal leaflets are normally 55 mm (l)×25 mm (w).

*Abundance.*—Generally, there are 2 leaves per 10 cm of stem.

*Leaf color.*—The upper surfaces of mature leaflets are Yellow-Green Group 146 A while the lower surfaces are Yellow-Green Group 147C. Upper surfaces of juvenile leaflets are are Yellow-Green Group 144A while the lower surfaces are Yellow-Green Group 144A.

*Stipules.*—Absent.

*Petioles.*—Size: Normally 30 to 35 mm in length by 1 mm diameter. Texture: Smooth. Color: Yellow-Green Group 144A with intonations of Greyed-Red Group 178A.

*Petioloule.*—Size: Normally 50 mm in length by 1 mm diameter. Texture: Smooth. Color: Yellow-Green Group 144A with intonations of Greyed-Red Group 178A.

*Leaflet shape.*—Generally elliptic. The base is oblique. The apex is acute.

*Margin.*—Entire.

*Surface.*—The upper side is smooth. The lower side is smooth.

*Thickness.*—Moderate.

*Glossiness.*—Glossy.

Disease resistance: Subject to any disease that normally attacks the species. However the variety is more tolerant to *clematis* wilt than some *clematis*.

We claim:

1. A new and distinct variety of *clematis* plant named 'Evipo041', substantially as described and illustrated, due to its abundant light pink flowers with good keepability, attractive foliage, compact growth, suitability for production from softwood cuttings in pots, durable flowers and foliage, which make the variety suitable for distribution in the floral industry.

* * * * *